United States Patent
Boukherroub et al.

(10) Patent No.: US 6,677,163 B1
(45) Date of Patent: Jan. 13, 2004

(54) FUNCTIONALIZED SILICON SURFACES, AND METHOD FOR THEIR PRODUCTION

(75) Inventors: Rabah Boukherroub, Ottawa (CA); Danial D. M. Wayner, Ottawa (CA); James Wojtyk, Ottawa (CA)

(73) Assignee: National Research Council of Canada, Ottawa (CA)

(*) Notice: Subject to any disclaimer, the term of this patent is extended or adjusted under 35 U.S.C. 154(b) by 0 days.

(21) Appl. No.: 09/713,300

(22) Filed: Nov. 16, 2000

(51) Int. Cl.$^7$ .................. G01N 33/552; C12Q 1/68; C12N 11/14; C07K 17/14
(52) U.S. Cl. .................. 436/527; 435/6; 435/181; 436/823; 530/391.1; 530/402; 530/408; 530/409; 530/410
(58) Field of Search .................. 436/527, 823; 530/391.1, 402, 408, 409, 410; 435/6, 181

(56) References Cited

U.S. PATENT DOCUMENTS

| | | | |
|---|---|---|---|
| 5,017,540 A | 5/1991 | Sandoval et al. | 502/158 |
| 5,326,738 A | 7/1994 | Sandoval et al. | 502/401 |
| 5,359,112 A | * 10/1994 | Drake | |
| 5,429,708 A | 7/1995 | Linford et al. | 216/66 |
| 5,773,308 A | 6/1998 | Conrad et al. | 436/527 |
| 5,843,767 A | 12/1998 | Beattie | 435/287.1 |

OTHER PUBLICATIONS

Boukherroub, Rabah, et al.: "Insights into the Formation Mechanisms of Si–OR Monolayers from the Thermal Reactions of Alcohols and Aldehydes with Si(111)H$^1$". National Research Council of Canada, Ottawa.
Lu, Wuyuan et al.: "Comparative Total Syntheses of Turkey Ovomucoid Third Domain by Both Stepwise Solid Phase Peptide Synthesis and Native Chemical Ligation." J. Am. Chem. Soc. 1996, 118, 8518–8523.
Stewart, Michael P.: "Chemical and Biological Applications of Porous Silicon Technology." Advanced Materials, 2000, 12, No. 12.
Xia, Younan et al.: "Soft Lithography". Agnew, Chem. Int. Ed. 1998, 37, 550–575.
Buriak, Jillian M. et al.: "Lewis Acid Mediated Functionalization of Porous Silicon with Substituted Alkenes and Alkynes". Am. Chem. Soc., 1998, 120, 1339–1340.
Boukherroub, R. et al.: "New Synthetic Routes to Alkyl Monolayers on the (111) Surface". Am. Chem. Soc., Langmuir, 1999, 15, 3831–3835.
Bansal, Ashish et al.: "Alkylation of Si Surfaces Using a Two–Step Halogenation/Grignard Route". J. Am. Chem. Soc. 1996, 118, 7225–7226.
Bergerson, W.F. et al.: "Assembly of Organic Molecules on Silicon Surfaces via the Si–N Linkage". J. Am. Chem. 1999, 121, 454–455.
Zhu, X. Y. et al. "Chemical Vapor Deposition of Organic Monolayers on Si(100) via Si–N Linkages ". J. Am. Chem. Soc. Langmuir, 1999, 15, 8147–8154.
Zhu, X. Y. et al. "Molecular Assemblies on Silicon Surfaces via Si–O Linkages". Am. Chem. Soc. Feb. 14, 2000.
Dancil, Keiki–Pua S. et al.: "A Porous Silicon Optical Biosensor: Detection of Reversible Binding of IgG to a Protein A–Modified Surface". J. Am. Chem. Soc. 1999, 121, 7925–7930.
Strother, Todd et al: "Synthesis and Characterization of DNA–Modified Silicon(111) Surfaces". J. Am. Chem. Soc. 2000, 122, 1205–1209.
Bateman, James E. et al.: "Alkylation of Porous Silicon by Direct Reaction with Alkenes and Alkynes". Angew, Chem. Int. Ed., 1998, 37, No. 19, 2683–2685.
Boukherroub, Rabah et al.: "Controlled Functionalization and Multistep Chemical Manipulation of Covalently Modified Si(111) Surfaces". J. Am. Chem. Soc., 1999, 121, 11513–11515.
Cullis, A.G.; Canham, L.T.; Calcott, P.D.J.; "The structural and luminescence properties of porous silicon" J. Appl. Phys. Lett. 1997, 82, 909–965.
Effenberger, F.; Gotz, G.; Bidlingmaier, B.; Wezstein, M.; "Photoactivated Preparation and Patterning of Self–Assembled Monolayers with 1–Alkenes and Aldehydes on Silicon Hydride Surfaces" Angew, Chem. Int. Ed. 1998, 37, No. 18, 2462–2464.
Sieval, A.B.; Demirel, A.L.; Nissink, J.W.M.; Linford, M.R.; Maas, J.H. van der.; Jeu, W.H. de.; Zuilhof, H.; Sudholter, E.J.R.; "Highly Stable Si–C Linked Functionalized Monolayers on the Silicon (100) Surface" Langmuir, 1998, 14, 1759–1768.
Wagner, P.; Nock, S.; Spudich, J.A., Volkmuth, W.D.; Chu, S.; Cicero, R.L.; Wade, C.P. Linford, M.R.; Chidsey, C.E.D.; "Bioreactive Self–Assembled Monolayers on Hydrogen–Passivated Si(111) as a New Class of Atomically Flat Substrates for Biological Scanning Probe Microscopy" J. Struct. Biol. 1997, 119, 189–201.

* cited by examiner

Primary Examiner—Mary E. Geperley (57) ABSTRACT

Provided is a method for modifying silicon with an organic molecule, under mild conditions. If the attached molecule is bi-functional, it may be subsequently reacted with a biomolecule, to form a covalently attached layer of biomolecule on the silicon surface.

6 Claims, 8 Drawing Sheets

FUNCTIONALIZED SILICON SURFACES, AND METHOD FOR THEIR PRODUCTION

FIELD OF THE INVENTION

The invention relates to the field of modified surfaces, more particularly to silicon surfaces modified with functionalised molecules.

BACKGROUND OF THE INVENTION

The covalent attachment of organic monolayers to semiconductor surfaces provides a route to passivation and a method to incorporate chemical and biochemical function into solid-state devices to produce bio-sensors or bio-sensor arrays.

Particularly sought after are methods for immobilising bio-molecules with specific binding functions, such as proteins or DNA, on silicon surfaces.

Several methods have been proposed for the preparation of organic layers on silicon surfaces, attached through Si—C and Si—O—C bonds. The relative susceptibility to hydrolysis of the Si—O—C bond is a disadvantage of this type of linkage for applications in which an aqueous environment is encountered.

Hydrogen terminated silicon is interesting as a substrate for immobilisation of organic molecules. Chidsey et al. demonstrated that the Si(111)H surface formed by etching with fluoride may be hydrosilylated by immersion in a neat alkene followed by irradiation[1]. Similar work is disclosed in U.S. Pat. No. 5,429,708 (to Linford et al., issued Jul. 4, 1995). The layers formed are extremely durable.

Bateman et al. have reacted hydrogen-terminated porous silicon surfaces thermally with 1-octene, 1-octyne, 1-undecene and vinyl ferrocene, by refluxing in toluene at 110–180° C. The surface-attached ferrocene moiety may be observed by cyclic voltammetry[2]. Boukherroub et al. use a modification of the method of Buriak et al. to achieve the modification of porous silicon by etching the silicon surface with ammonium fluoride to form a hydrogen-terminated Si(111) surface, followed by hydrosilylation with an alkene in the presence of a Lewis acid catalyst $(AlEtCl_2)$[3,4].

Sieval et al. report the thermal reaction of alkenes terminated with ester groups, with an Si(100) hydrogen terminated surface[5]. The ester groups can be hydrolysed to release a carboxylic acid-modified surface, or reduced with $LiAlH_4$ to produce an alcohol-modified surface. Re-esterification of either of these surfaces by refluxing with an alcohol or carboxylic acid, respectively, in the presence of acid catalyst is possible. The required conditions are unfortunately too harsh to be compatible with most biological molecules.

Hydrogen-terminated Si(100) and Si(111) modified through Si—O linkages have been reported by Zhu et al. A silicon substrate is etched with $NH_4F$, to produced a hydrogen-terminated surface. Exposure of the surface to gaseous chlorine results in a Cl-capped surface, which is subsequently reacted with dodecanol or octadecanol to produce $C_{12}$ and $C_{18}$ chains, respectively, immobilised on the Si surface by Si—O bonds[6]. Zhu et al. has reported a similar procedure, wherein a Cl-capped Si(100) surface is exposed to amine vapour, to produce amines attached to the silicon surface via two N—Si bonds[7]. They have reported the use of an analogous procedure to attach molecules to a clean Si(100) surface and a porous silicon surface via Si—N bonds[8].

Lewis et al. formed Si(111)—C linkages using a two-step method, whereby an Si(111) surface is first chlorinated, and then reacted with an alkyl Grignard or alkyl lithium reagent[9]. Boukherroub et al. have demonstrated that similar modification can be achieved by direct reaction of alkyl magnesium bromides with an Si(111) surface[10].

The photochemical hydrosilylation of aldehydes with an Si(111)—H surface, to form an Si(111)—OCH$_2$R surface has been reported by Effenberger et al[11].

Sailor et al. disclose modification of porous silicon with BSA or protein A via a complicated 8-step method. The linkage to the silicon surface is through an Si—O—Si linker on the oxidised (i.e. $SiO_2$) surface. Binding of IgG to surface bound protein A is measured by observing the shift in effective optical thickness using interferometry[12].

Strother et al. report the modification of Si(111) with non-covalently attached DNA. A hydrogen-terminated Si(111) surface is reacted with an ω-undecylenic acid methyl or trifluoroethyl ester by UV irradiation of a thin film of the ester applied to the surface. The ester functionality is hydrolysed by treatment with potassium t-butoxide in DMSO, to yield a carboxylic acid-modified surface. Polylysine is added, becoming immobilised on the surface through ionic interactions between the polylysine amino groups and the surface carboxylate groups. Thiol-modified DNA is then linked to the polylysine via the bi-functional linker sulfosuccinimidyl 4-(N-maleimidomethyl)-cyclohexane-1-carboxylate[13].

There remains to be found a simple, versatile method for durable covalent attachment of organic molecules to hydrogen-terminated silicon surfaces, under conditions that are compatible with bio-molecules.

SUMMARY OF THE INVENTION

It is an object of the invention to provide a method for immobilising molecules on a hydrogen-terminated silicon surface.

It is another object of the invention to provide a silicon surface with an immobilised layer which layer is suitable to be further reacted to attach a bio-molecule.

It is a further object of the invention to provide a silicon surface modified with a bio-molecule.

In a first aspect the invention provides a method for immobilising a desired molecule on a silicon substrate, the method comprising the steps:

(A) providing an Si—H surface on the silicon substrate; and (B) attaching the desired molecule to the Si—H surface via a covalent bond.

In a second aspect, the invention provides a method for providing a coupling group on a silicon substrate, the method comprising the steps:

(A) providing an Si—H surface on the silicon substrate;

(B) reacting the Si—H surface with a linker-molecule possessing at least one anchor functionality capable of reacting with the Si—H surface to form an Si—C or Si—O linkage, and further possessing at least one coupling group and/or protected coupling group which does not react with the Si—H surface; and (C) removing unreacted linker-molecule.

In a third aspect, the invention provides a method for immobilising a desired molecule on a silicon substrate, the method comprising the steps:

(A) providing an Si—H surface on the silicon substrate;

(B) reacting the Si—H surface with a linker-molecule possessing at least one anchor functionality capable of reacting with the Si—H surface to form an Si—C or Si—O linkage, and further possessing at least one coupling group and/or protected coupling group which does not react with the Si—H surface;

(C) removing unreacted linker-molecule;

(D) if a protected coupling group is present, deprotecting the protected coupling group; and (E) reacting the coupling group with the desired molecule.

In a fourth aspect, the invention provides a silicon substrate bearing immobilised coupling groups attached to the silicon substrate by Si—C bonds or Si—O bonds.

In a fifth aspect, the invention provides a silicon substrate bearing a bio-molecule attached to the silicon substrate covalently via Si—C bonds or Si—O bonds.

DETAILED DESCRIPTION OF THE INVENTION

BRIEF DESCRIPTION OF THE DRAWINGS

The invention is illustrated in some preferred embodiments with the aid of the drawings.

The method of the invention, in the first aspect, provides coupling groups on the surface of a silicon substrate by reacting a bi-functional linker molecule with a hydrogen-terminated surface of a silicon substrate. The linker molecule is preferably attached to the substrate via a C—Si linkage, which is known to be as strong as a C—C bond, and is chemically robust.

The preferred silicon substrates are porous silicon, particularly Si(100), or single crystal silicon, preferably Si(111) or Si(100). This includes both n- and p-type silicon, at any doping level. Porous silicon is particularly attractive, as its high surface area allows a high density of modification. For a discussion of porous silicon, including methods for its preparation, see *The structural and luminescent properties of porous silicon* by Cullis et al.[14], incorporated herein by reference.

Hydrogen-terminated surfaces may be produced on a silicon substrate using various techniques, including plasma reduction, etching with HF, electrochemical etching, and etching with ammonium fluoride[15, 16]. A particularly good method is to treat silicon with a strong oxidising agent, for example 3:1 $H_2SO_4$:30% $H_2O_2$, followed by etching with 40% ammonium fluoride, to produce a hydrogen-terminated surface.

A desired molecule may be attached to the Si surface in many different ways. Covalent bonds with the Si—H surface may be formed by reaction of the Si—H group with an anchor group selected from ethenyl (preferably terminal), ethynyl (preferable terminal), carbonyl (for example CHO or RCOR'), OH, $NH_2$ and SH. If the desired molecule itself possesses one of these functionalities, it can be reacted with the Si—H surface directly. If the desired molecule does not posses one of these functionalities, a linker molecule may be used.

If a linker molecule is used, the linker molecule must possess at least one anchor group that is capable of reacting with the SiH surface. Preferred anchor groups are ethenyl (preferably terminal), ethynyl (preferable terminal), carbonyl (for example CHO or RCOR'), OH, $NH_2$ and SH. The groups OH, $NH_2$ and SH react with the SiH surface through oxidative addition, whereas the other groups react through hydrosilylation. Preferred groups are ethenyl and ethynyl. The groups ethenyl and ethynyl form Si—C linkages with the silicon surface. The groups CHO, RCOR' and OH form Si—O—C linkages with the silicon surface. Si—O—C linkages are less resistant to hydrolysis than Si—C linkages. For uses in which prolonged contact with aqueous media is expected, Si—C linkages are preferred.

The reaction between the anchor group and the SiH surface may be induced thermally, photochemically, or with a catalyst (for example a Lewis acid, such as $AlEtCl_{12}$). The inventors have found that with a catalyst, lower surface coverage of the linker molecule is obtained[17]. The use of a catalyst also potentially introduces contaminants to the surface, which are undesirable for uses in which surface homogeneity and predictability is required, for example when constructing a micro-array. It is therefore preferred to induce reaction between the linker molecule and the surface using UV irradiation or thermally (i.e. by heating). The inventors have found that better coverage is usually obtained when the reaction is carried out thermally.

The reaction between the anchor group and the SiH surface may be carried out with the substrate immersed in a solution of the linker molecule in a solvent (for example benzene, toluene, or a hydrocarbon, such as hexane, heptane, etc.). The reaction may also be a carried out simply by covering the substrate, or a portion of the substrate with the linker molecule (in the liquid state), and initiating with heat, UV-radiation or a catalyst. The reaction may further be carried out in the gas phase, by maintaining the substrate in an atmosphere comprising the linker molecule in the gaseous state.

After reaction between the substrate SiH surface and the linker molecule, any linker molecule which does not react with the SiH surface may be removed by rinsing the substrate with a suitable solvent (for example 1,1,1-trichloroethane). The modified substrate may then be dried under a stream of gas (for example argon or nitrogen), or it may be air dried.

The linker molecule also carries at least one coupling group which does not react with the SiH surface. The coupling group may be any group which is capable of reacting with another organic molecule under relatively mild conditions to form one or more covalent bonds. The coupling group may also be a group which is protected with a protecting group, and which upon deprotection reveals a coupling group ready to react with a suitable reagent. Examples of coupling group and protected coupling group which may be used include carboxyl, protected carboxyl [for example methyl ester, 9-fluorenylmethyl ester, methoxymethyl ester, methylthiomethyl ester, tertrahydropyranyl ester, 2-(trimethylsilyl)ethoxymethyl ester, benzyloxymethyl ester, triisopropylmethylsilyl ester, cyanomethyl ester, N-phthalimidomethyl ester, 2,2,2-trichloroethyl ester, bis(o-nitrophenyl)methyl ester, triethylsilyl ester, t-butyldimethylsilyl ester, etc.], acyl halides (for example acyl chlorides or bromides), amino, protected amino [for example 9-fluorenylmethyl carbamate (Fmoc), 2,2,2-trichloroethyl carbamate (Troc), t-butyl carbamate (BOC), 1-adamantyl carbamate (1-Adoc), (m, o, or p)-nitrophenyl carbamates, 3,5-dimethoxybenzyl carbamate, etc.] activated esters (such as N-succinimido, trifluoroethyl, m-, o- and p-nitrophenol, thioesters), protected hydroxyl [for example methyl ether, methoxymethyl ether, methylthiomethyl ether, tetrahydrofuranyl ether, trimethylsilyl ether, formate ester, benzoylformate ester, acetate ester, etc.], thiol and protected thiol (for example Alkyl thioether, 9-fluorenylmethyl thioether, thioesters, etc.). Particularly preferred are activated carboxylates, since after modification of the surface, coupling can be carried out directly.

Examples of some activated carboxylates are those compounds made by the reaction of a carboxylate with 1,1'-carbonyldiimidazole ("imidazolides"), and N-hydroxysuccinimide (N-succinimido). Such activated carboxylates are reacted with alcohols, to produce esters, or with amines, to produce amides.

Some examples of protecting groups for coupling groups are as follows:

carboxy: methyl ester, methoxymethyl ester, tetrahydropyran ester, phenacyl ester, t-butyl ester, triphenyl methyl ester, piperonyl;

hydroxy: formate ester, acetate ester, chloroacetate ester, phenoxyacetate ester, pivalate ester, benzoate ester, methyl carbonate, N-phenyl carbamate;

thiol: 5-benzyl, 5-diphenyl methyl, S-t-butyl, S-benzoyl, methoxybenzylthioether;

amino: fluororenyl methoxy carbonyl (FMOC), t-butyloxycarbonyl (t-BOC), allyl carbamate (alloc), carbamoyl, carbobenzyloxy (CBZ).

Other appropriate protecting groups will be known to one skilled in the art, for example see "Protective groups in organic synthesis"; Theodora W. Greene and Peter G. M. Wuts; New York, Wiley 1999 (incorporated herein by reference).

The linker molecule may have more than one anchor group, however, more orderly covering layers are produced with a single anchor group per molecule.

The linker molecule may also have more than one coupling group. Again, more orderly coverage with a second molecule during coupling is obtained when a single coupling group is present.

Reaction between a linker molecule coupling group and a desired molecule may be carried out after attachment of the linker molecule to the silicon surface, or the desired molecule may first be reacted with the coupling group to form a [linker molecule-desired molecule] conjugate, and the conjugate can then be reacted with the Si surface.

The "skeleton" of the linker molecule, that is the portion other than the anchor group and the coupling group, is not particularly limited in structure, provided it does not posses any groups which would interfere either with the "anchoring reaction" (attachment to the Si surface) or a coupling reaction. Examples include alkylene skeletons, bearing the anchor group terminally at one end, and the coupling group terminally at the other end. Amongst alkylene skeletons, medium to long chain ($C_{6-18}$) alkylene are more preferred, because they pack well on the Si surface. An additional example is oligopolythylenelycol (oligoPEG) skeleton. PEG is known to inhibit protein absorption and adhesion on surfaces. An Si surface patterned with PEG-type molecules, using the patterning methods described below, exhibits selective protein absorption.

The method of the invention is versatile, and allows attachment of a great variety of molecules to the silicon substrate. When the substrate is modified with a linker molecule, the result is a layer of immobilised coupling groups or immobilised protected coupling groups on the silicon surface. The modified substrate may then be stored until it is desired to further functionalise the surface, at which time a coupling reaction can be carried out involving the immobilised coupling groups (deprotected, if necessary) and an organic molecule.

If a protected coupling group is used, the protecting group must be removed for further functionalisation of the substrate. Examples of protecting groups, and methods for removing protecting groups are shown in Table 1.

TABLE 1

Examples of protected coupling groups which can be immobilised on the Si surface

| Protected coupling group | Deprotected coupling group | example of method to remove | reference (incorporated herein by reference) |
| --- | --- | --- | --- |
| ![structure: acetate ester of m-nitrophenol] | COOH | light (<300 nm) | |
| —COOMe | COOH | LiOH, $CH_3OH/H_2O$ | Corey et al.; Tetrahedron Lett., 3529 (1977) |
| 9-fluroenylmethyl Ester (Fm) | COOH | Diethylamine or piperidine in $CH_2Cl_2$ | Kessler et al.; Tetrahedron Lett., 24, 281 (1983) |

TABLE 1-continued

Examples of protected coupling groups which can be immobilised on the Si surface

| Protected coupling group | Deprotected coupling group | example of method to remove | reference (incorporated herein by reference) |
|---|---|---|---|
| Methoxymethyl Ester (MOM) | COOH | $MgBr_2$, $Et_2O$; or Pyr, $H_2O$ | Kim et al.; Tetrahedron Lett., 32, 3099 (1991); Shimano et al.; Chem. Pharm. Bull., 38, 276 (1990) |
| Methylthiomethyl Ester (MTM) | COOH | $CF_3COOH$; or $HCl/Et_2O$ | Ho et al.; J. Chem. Soc., Chem. Commun., 224 (1973); Dossena et al.; Int. J. Pep. Prot. Res. 23, 198 (1984) |
| Tetrahydropyranyl Ester (THP) | COOH | AcOH, THF, $H_2O$, 45° C., 3.5 hr. | Bernady et al.; J. Org. Chem., 44, 1438 (1979) |
| Benzyloxymethyl Ester (BOM) | COOH | Aqueous HCl, THF, 25° C., 2 hr. | Zoretic et al.; J. Org. Chem., 40, 2962 (1975) |
| Triisopropylmethyl silyl Ester | COOH | 3 N NaOH, reflux | Soderquist et al.; Tetrahedron Lett, 34, 4905 (1993) |
| cyanomethyl Ester | COOH | $Na_2S$, acetone, water | Hugel et al.; Synth. Commun., 22, 693 (1992) |
| N-phthalimidomethyl Ester | COOH | $H_2NNH_2$/MeOH, 20° C., 3 h | Nefkens et al.; Recl. Trav. Chim. Pays-Bas, 82, 941 |
| 2,2,2-trichloroethyl Ester | COOH | electrolysis: -1.65 V VS $LiClO_4$, MeOH | Semmelhack et al.; J. Am. Chem. Soc., 94, 5139 (1972) |
| bis(o-nitrophenyl)methyl Ester | COOH | hν = 320 nm, dioxane, THF | Patchornik et al; J. Am. Chem. Soc., 92, 6333 (1970) |
| 1-pyrenylmethyl Ester | COOH | hν = 340 nm | Iwamura et al; Tetrahedron Lett., 28, 679 (1987) |
| Triethylsilyl Ester | COOH | AcOH, $H_2O$, THF, 20° C., 4 h | Hart et al; J. Chem. Soc., Chem. Commun., 156 (1979) |
| t-butyldimethyl silyl Ester | COOH | $K_2CO_3$, MeOH, $H_2O$, 25° C., 1 h | Morton et al.; J. Org. Chem., 43, 2102 (1978) |
| 9-fluorenylmethyl carbamate (Fmoc-N) | $NH_2$ | piperidine, DMF | Atherton et al.; "The Fluorenylmethoxycarbonyl Amino Protecting group"; in The Peptides, Academic Press, New york, 1987 Volume 9, pg. 1 |
| 9-(2,7-dibromo) fluorenylmethyl carbamate | $NH_2$ | Pyridine | Carpino; J. Org. Chem.; 45, 4250 (1980) |
| 2,2,2-trichloroethyl carbamate | $NH_2$ | electrolysis: -1.7 V, 0.1 M $LiClO_4$ | Semmelhack et al; J. Am. Chem. Soc., 94, 5139 (1972) |
| t-butyl carbamate (t-BOC-N) | $NH_2$ | 3 M HCl, EtOAc, 25° C., 30 min. | Stahl et al.; J. Org. Chem., 43, 2285 (1978) |
| 1-adamantyl carbamate | $NH_2$ | $CF_3COOH$, 25° C., 15 min. | Haas et al.; J. Am. Chem. Soc., 88, 1988 (1966) |
| m-nitrophenyl carbamate | $NH_2$ | Photolysis | Wieland et al.; Makromol. Chem., 92, 277 (1966) |
| 3,5-dimethoxybenzyl carbamate | $NH_2$ | Photolysis | Chamberlin; J. Org. Chem., 31, 1658 (1966) |
| α-methylnitropiperonyl carbamate | $NH_2$ | Photolysis | Holmes et al.; Pept.: Chem., Struct. Biol., Proc. Am. Pept. Symp., 13th, 110 (1994) |
| o-nitrobenzyl carbamate | $NH_2$ | Photolysis | Amit et al.; J. Org. Chem., 39, 192 (1974) |
| 3,4-dimethoxy-6-nitrobenzyl carbamate | $NH_2$ | Photolysis | Burgess et al.; J. Org. Chem., 62, 5165 (1997); and Amit et al.; J. Org. Chem., 39, 192 (1974) |
| Phenyl(o-nitrophenyl)-methyl carbamate | $NH_2$ | Photolysis | Baltrop et al.; J. Chem. Soc., Chem. Commun., 822 (1966) |
| 2-(2-nitrophenyl)ethyl carbamate | $NH_2$ | Photolysis | Hasan et al.; Tetrahedron, 53, 4247, (1997) |
| 6-nitroveratryl carbamate | $NH_2$ | Photolysis | Rollins et al.; Tetrahedron Lett., 38, 4033 (1997) |
| 4-methoxyphenacyl carbamate | $NH_2$ | Photolysis | Church et al.; Tetrahedron L:ett.; 30, 1901 (1989) |
| —OMe | OH | $Me_3SiI$, $CHCl_3$, 25° C., 6 h | Jung et al.; J. Org. Chem., 42, 3761 (1977) |

TABLE 1-continued

Examples of protected coupling groups which can be immobilised on the Si surface

| Protected coupling group | Deprotected coupling group | example of method to remove | reference (incorporated herein by reference) |
|---|---|---|---|
| Methoxymethyl ether (MOM) | OH | Trace conc. HCl, MeOH, 62° C., 15 min. | Auerbach et al.; J. Chem. Soc., Chem. Commun., 298 (1974) |
| Tetrahydropyranyl ether (THP) | OH | AcOH, THF, $H_2O$, 45° C., 3.5 h | Corey et al.; J. Am. Chem. Soc., 100, 8031 (1978) |
| 1-ethoxyethyl ether | OH | 5% AcOH, 20° C., 2 h | Chládek et al.; Chem. Ind. (London), 1719 (1964) |
| t-butyl ether | OH | anhydrous $CF_3COOH$ | Callahan et al.; J. Am. Chem. Soc., 85, 201 (1963) |
| Tetrahydrofuranyl ether | OH | AcOH, $H_2O$, THF, 25° C., 30 min. | Kruse et al.; Recl. Trav. Chim. Pays-Bas, 98, 371 (1979) |
| acetate ester | OH | $K_2CO_3$/MeOH, $H_2O$, 20° C., 1 h; guanidine, EtOH, $CH_2Cl_2$, RT; $H_2NNH_2$, MeOH; | Plattner et al.; J. Am. Chem. Soc., 94, 8613 (1972) Kunesch et al.; Tetrahedron Lett. 28, 3569 (1987); Roush et al.; J. Am. Chem. Soc., 117, 2236 (1995); |
| Trichloroacetate ester | OH | $NH_3$, EtOH, $CHCl_3$, 20° C., 6 h | Schwarz et al.; Collect. Czech. Chem. Commun., 27, 2567 (1962) |
| Trifluoroacetate ester | OH | $H_2O$, pH 7, 20° C. | Cramer et al; Tetrahedron Lett., 1039 (1963) |
| Methoxy acetate ester | OH | $NH_3$/MeOH or $NH_3/H_2O$ | Reese et al.; Tetrahedron Lett., 4273 (1968) |
| Phenoxy acetate ester | OH | t-$BuNH_2$, MeOH | Reese et al.; Tetrahedron Lett., 4273 (1968) |
| Methoxymethyl carbonate | OH | $K_2CO_3$, MeOH, $H_2O$, 30 min., 20° C. | Teranishi et al.; Synthesis, 176 (1995) |
| 2,2,2-trichloroethyl carbonate | OH | electrolysis: −1.65 V, MeOH, $LiClO_4$ | Semmelhack et al.; J. Am. Chem. Soc., 94, 5139 (1972) |
| 3',5'-dimethoxybenzoin carbonate | OH | Photolysis | Pirrung et al.; J. Org. Chem., 60, 1116 (1995) |
| Methane sulfonate ester | OH | photolysis, KI, MeOH | Binkley et al.; J. Carbohydrate Res., 11, 1053 (1992) |
| 9-fluorenylmethyl carbonate | OH | $Et_3N$, Pyr, 2 h | Gioeli et al.; J. Chem. Soc. Chem. Commun., 672 (1982) |

Methods for creating patterns on a surface at the microscopic level are known in the art (see, for example Whitesides et al.; *Soft Lithography; Angew. Chem. Int. Ed.* 1998, 37, 550–575, and references therein; incorporated herein by reference). Such methods can be modified for use with the method of the invention. Paterning can be used to produce surfaces with modified and unmodified areas, or areas modified with different functionalities. Patterning of the Si surface is possible at different stages during the method of the invention.

For example, the linker molecule, or a solution of the linker molecule may be "painted" onto specific areas of the substrate or applied through a mask, in order to create a pattern of linker molecule. When reaction is initiated between the SiH surface and the linker molecule, a pattern of modified/unmodified areas will be created on the surface. Alternatively, the linker molecule may be applied uniformly on the surface of the substrate, and patterning may be introduced as follows:

1. A second molecule, capable of reacting with the coupling group, may be applied to selected areas of the linker molecule-modified substrate, either by painting or by the use of a mask;
2. If a linker molecule is used in which the coupling group is an activated ester, the activating group may be selectively removed in a patterned fashion. For example, a surface-bound carboxyl group, protected as a m-nitrophenol ester, may be cleaved with UV light of wavelength less than about 300 nm. The substrate, modified with a linker molecule bearing the activating m-nitrophenol ester group is exposed to UV light through a mask, to produce a pattern of free carboxylate/activated ester areas. Alternatively, a high resolution beam of UV light can be used to trace a pattern of free carboxylate/activated ester areas on the surface. Subsequent reaction of the surface-bound activated ester groups with an amine or alcohol results in a pattern of amide or ester derivatisation on the surface.

Alternatively, a linker molecule may be used which bears a coupling group protected with a photolabile protecting group, for example a carboxylate protected as a 1-pyrenylmethyl ester. Irradiation of portions of the surface with light of the appropriate wave length results in a surface having areas that bear free carboxylates and areas that bear protected carboxylates. Reaction of the free carboxylates with an amine or an alcohol, in the presence of a coupling agent [for example, dicyclohexylcarbodiimide (DCC), hydroxybenzotriazole (HOBT), diisopropylcarbodiimide (DIC), O-(7-azabenzotriazol-1-yl)-N,N,N',N'-tetramethyluronium hexafluorophosphate (HATU!), 2-(1-H-benzotriazol-1-yl)-1,1,3,3-tetramethyluronium hexafluorophosphate (HBTU)], and optionally in the presence of a non-nucleophilic base [for example, N,N-diisopropyl-ethylamine (DIEA), N-ethylmorpholine, pyridine or triethylamine], results in a surface bearing a pattern of amide or ester derivatisation.

The linker molecule may be applied as a single component layer to the substrate surface, or it may be diluted, with another molecule (bearing an anchor group), the other molecule either bearing a coupling group of different specificity than the linker molecule, or bearing no reactive functionality (under the conditions used). This results in a layer on the substrate in which the coupling groups are spaced apart, rather than being tightly packed. The inventors have found that when mixtures of functionalised and non-functionalised molecules are used, the distribution on the surface of the two kinds of molecules is stoichiometric This means that surfaces can be prepared in which the spacing between coupling groups can be carefully controlled, merely by diluting the linker molecule to the desired extent, with another molecule bearing no additional functionality.

Some examples of how molecules may be attached to the Si surface, and how patterns may be formed, are as follows:

In the following discussion, the following definitions apply:

X is a group capable of reacting with the Si surface to form a covalent bond (e.g. ethenyl (preferably terminal), ethynyl (preferable terminal), carbonyl (for example CHO or RCOR'), OH, $NH_2$ and SH);

S is a spacer group;

U is an unactivated functionality;

AG is an activated functionality;

P is a protecting group;

BM is a biomolecule;

W is the Si surface; and

D is a deactivated group which insulates the surface from further reactions.

Some illustrations of possible surface-modification protocols are:

1. react X-S-BM or X-BM with surface (W) W-X-S-BM or W-X-BM;
2. react X-S-AG or X-AG with surface (W) W-X-S-AG or W-X-AG; then react with biomolecule (BM) W-X-S-BM or W-X-BM; then deactivate unreacted (AG) regions with D W-X-S-D or W-X-D; resulting in areas of D and areas of BM on the surface;
3. react X-S-U with the surface (W) W-X-S-U; activate U W-X-S-AG; react with biomolecule (BM) W-X-S-BM;
4. react X-S-P with surface (W) W-X-S-P; deprotect W-X-S-U; activate W-X-S-AG; react with biomolecule (BM) W-X-S-BM;
5. react X-S-P with the surface (W) W-X-S-P; deprotect part of the surface W-X-S-U (with areas of W-X-S-P); activate W-X-S-AG (with areas of W-X-S-P); react with biomolecule W-X-S-BM (with areas of W-X-S-P); this can be repeated by deprotecting more areas, activating and reacting with other biomolecules, to build an array of different biomolecules on the surface;
6. react X-S-U with surface W-X-S-U; protect part of the surface W-X-S-P (with areas of W-X-S-U); activate unprotected areas of surface W-X-S-AG (with areas of W-X-S-P); react activated area of surface with biomolecule W-X-S-BM (with areas of W-X-S-P); deprotect, activate and react with other biomolecules, to build an array of different biomolecules on the surface;
7. react X-S-AG with surface W-X-S-AG; react part of the surface area with a biomolecule, part of the surface area with a different biomolecule, repeat to build an array of different biomolecules on the surface.

In any of protocols 1 to 7, the spacer group is optional. Also, in any of protocols 1 to 7, unreacted surface or surface attached molecules may be deactivated by reaction with a deactivating group, D.

Any molecule capable of reacting with a surface-attached coupling group, may be immobilised on the substrate. In a preferred embodiment, bio-molecules are attached. For the purposes of this description, the expression bio-molecule is meant to encompass any molecule natural or artificial, which produces, or has the potential to produce, a biological/physiological response or to interact specifically with any other bio-molecule. Examples are DNA, RNA, proteins (such as enzymes, hormones, antibodies, antibody fragments), carbohydrates or conjugates of these molecules. Also included are libraries of these molecules for the purposes of screening/monitoring/manipulating biological activity.

An appropriate match between coupling group and the bio-molecule must be chosen. For example, single stranded DNA, modified with an amine group, can be immobilised using a carboxyl or activated carboxyl coupling group, to form an amide linkage. Alternatively, DNA may be immobilised directly by reaction of the 3' or 5' hydroxyl with a carboxylate group on the surface.

Proteins can be immobilised by reaction of their free amino groups with carboxyl groups on the surface (either activated carboxyl groups, or carboxyl groups in the presence of a coupling reagent), by thiol exchange of their cysteine thiol groups or methionine mercapto groups with alkylthio groups on the surface, by reaction of their carboxyl groups with amino groups on the surface (either activated carboxyl groups, or carboxyl groups in the presence of a coupling reagent), etc. Immobilised bio-molecules serve as receptor elements for bio-sensor devices. For example, a DNA probe complementary to a target sequence can be immobilised, and used to analyse for the target sequence in a mixture. Hybridisation of the target sequence can be detected in a variety of ways. The target strand can be amplified using PCR with primers that are biotinylated. The resulting amplified DNA bears biotin. After hybridisation has occurred with the immobilised probe, a streptavidin-enzyme conjugate is added (for example streptavidin-alkaline phosphatase, or streptavidin-luciferin), and hybridisation is visualised using an appropriate substrate. Alternatively, a radioactive label can be incorporated into the amplified DNA, or the DNA may be labelled with a fluorescent probe.

The techniques mentioned above for DNA apply equally well to proteins with specific binding functions.

The homogeneity of layers formed on an SiH surface, using the method of the invention, is such that the construction of microarrays with very high resolution is possible. The method of the invention is particularly suited to multiple probe analysis of DNA binding. For example, using patterning methods, different DNA probes are attached to the surface in a matrix. The surface is then contacted with a mixture of labelled amplified target sequences. After hybridisation has occurred, the matrix may be inspected (for example using a high resolution optical technique, such as laser confocal microscopy). This allows analysis using a large number of probes on a small surface area.

The Si surface can also be used for solid-phase synthesis, and is particularly suited to combinatorial methods. For example, an N-protected amino acid may be attached to the hydrogen-terminated Si surface, for example, by attachment of an amino-bearing linker molecule to the surface, followed by reaction of the carboxyl group of a protected amino acid with surface attached amino groups. Deprotection followed by coupling with a second, suitably protected, amino acid is then carried out. These cycles can be repeated, building a chain of amino acids on the Si surface.

Specific Embodiments

EXAMPLES

Materials. All chemicals were reagent grade or higher and used as received unless otherwise specified. Ultrapure water was obtained from a Millipore system (resistivity ~18 mΩ). 1-Decene, n-butylamine, undecylenic acid, 2,2,2-trifluoroethanol, 3-nitrophenol, N-hydroxysuccinimide, ethanethiol, n-butylamine, 4-dimethylaminopyridine (DMAP), dithiothreitol (DTT) and 1,3-di-n-isopropylcarbodiimide (DIC) were all available from Aldrich. The methyl esters of L-alanine (Me-Ala) and L-cysteine (Me-Cys) were purchased from Sigma. All solvents were obtained from VWR and distilled under an inert atmosphere. Tetrahydrofuran (THF) was passed through an activated column of alumina and refluxed over Na for 24 h prior to collecting. n-Heptane was washed with $H_2SO_4$, water and 10% $Na_2CO_3$ before distillation from Na. N,N-dimethylformamide (DMF) was distilled under reduced pressure while refluxing with $CaH_2$. Phosphate-buffered saline (PBS) solutions were obtained from Aldrich and the pH was adjusted with a 0.1 M KOH solution.

Synthesis of 3-nitrophenyl undecylenate (I): In a 100 mL round-bottom flask equipped with a magnetic stirrer and a nitrogen inlet, was placed undecylenic acid (1.00 g, 5.43 mmol) and 3-nitrophenol (0.83 g, 6.00 mmol). The mixture was dissolved in 10 mL of dry THF and cooled to 0° C. before a 10 mL THF solution of DIC (0.75 g, 6.00 mmol) and DMAP (0.073 g, 0.60 mmol) was added dropwise via a syringe over a 10 minute period. The mixture was gradually allowed to warm to room temperature and stirred at this temperature for 18 h. The urea by-product was filtered off and the filtrate concentrated to produce a crude solid that was recrystallized from EtOAc to produce a yellow solid, yield=1.24 g, 73%.

$^1$H-NMR (400.1 MHz) in $CDCl_3$: 8.13 (d, 1H, J=7.5 Hz), 8.03 (s, 1H), 7.55 (t, 1H, J=8.3), 7.44 (d, 1H, J=7.5 Hz), 5.70–5.90 (m, 1H), 4.86–5.06 (m, 2H), 2.35–2.45 (t, 2H), 1.98–2.10 (m, 2H), 1.70–1.82 (m, 2H), 1.20–1.50 (m, 10H). IR ($CCl_4$, cm$^{-1}$): 3023 (Vinyl-H), 2928, 2853 (C—H), 1765 (C=O), 1610 (C=C), 1532 ($NO_2$), 1351 ($NO_2$), 1211 (C—O).

Synthesis of N-Succinimidyl undecylenate (II): In a 100 mL round bottom flask equipped with a magnetic stirrer and a nitrogen inlet, were placed undecylenic acid (1.00 g, 5.43 mmol) and N-hydroxysuccinimide (0.69 g, 6.00 mmol). The mixture was dissolved in 5 mL of dry DMF and cooled to 0°C. before a 5 mL DMF solution of DIC (0.75 g, 6.00 mmol) and DMAP (0.073 g, 0.60 mmol) was added dropwise via a syringe over a 10 minute period. The mixture was warmed to room temperature and stirred for 18 h at this temperature. The urea by-product was filtered off and the filtrate concentrated to produce a crude solid. Flash chromatography (Rf: 0.5, $CH_2Cl_2$) of the mixture and concentration of the collected fractions produced a white solid, 1.57 g, 98%.

$^1$H-NMR (400.1 MHz) in DMSO-$d_6$: 5.70–5.90 (m, 1H), 4.86–5.06 (m, 2H), 2.85 (br s, 4H), 2.55–2.65 (t, 2H, J=7.5 Hz), 1.98–2.10 (m, 2H), 1.70–1.85 (m, 2H), 1.20–1.50 (m, 10H). IR ($CCl_4$, cm$^{-1}$): 3077 (Vinyl-H), 2928 (C—H), 2853 (C—H), 1819 (C=O), 1791 (C=O), 1749 (C=O), 1640 (C=C), 1462 ($CH_2$), 1160 (C=O).

Synthesis of S-Ethyl undecylenate (III): In a 100 mL round bottom flask equipped with a magnetic stirrer and a nitrogen inlet were placed undecylenic acid (1.00 g, 5.43 mmol) and ethanethiol (0.37 g, 6.00 mmol). The mixture was dissolved in 10 mL of dry THF and cooled to 0° C. before a 10 mL THF solution of DIC (0.75 g, 6.00 mmol) and DMAP (0.073 g, 0.60 mmol) was added dropwise via a syringe over a 10 minute period. The mixture was stirred for 18 h at 0° C. The urea by-product was filtered off and the filtrate concentrated to produce a crude product that was loaded onto a column of silica gel. Flash chromatography ($R_f$: 0.7, $CHCl_3$) of the mixture and concentration of the collected fractions produced a colorless oil, yield=1.07 g, 82%.

$^1$H-NMR (400.1 MHz) in $CDCl_3$: 5.70–5.90 (m, 1H), 4.86–5.06 (m, 2H), 2.80–2.95 (q, 2H, J=7.5 Hz), 2.48–2.59 (t, 2H, J=7.5 Hz), 1.98–2.10 (m, 2H), 1.60–1.75 (m, 2H), 1.20–1.50 (m, 10H).

IR (cm-1): 3077 (Vinyl-H), 2974 (C—H), 2928 (C—H), 2856 (C—H), 1692 (C=O), 1640 (C=C).

Synthesis of 2,2,2-Trifluoroethyl undecylenate (IV): In a 100 mL round bottom flask equipped with a magnetic stirrer and a nitrogen inlet, were placed undecylenic acid (1.00 g, 5.43 mmol) and 2,2,2-trifluoroethanol (0.60 g, 6.00 mmol). The mixture was dissolved in 10 mL of dry THF and cooled to 0°C. before a 10 mL THF solution of DIC (0.75 g, 6.00 mmol) and DMAP (0.073 g, 0.60 mmol) was added dropwise via a syringe over a 10 minute period. The mixture was gradually allowed to warm to room temperature and stirred at this temperature for 18h. The urea by-product was filtered off and the filtrate concentrated to produce a crude product that was loaded onto a column of silica gel. Flash chromatography (Rf=0.7, $CHCl_3$) of the mixture and concentration of the collected fractions produced a colorless oil, yield= 1.47 g, 83%.

$^1$H-NMR (400.1 MHz) in $CDCl_3$: 5.70–5.90 (m, 1H), 4.86–5.06 (m, 2H), 4.38–4.51 (q, 2H, J=8.5 Hz), 2.35–2.45 (t, 2H, J=7.5 Hz), 1.98–2.10 (m, 2H), 1.55–1.75 (m, 2H), 1.20–1.50 (m, 10H). IR ($CCl_4$, cm$^{-1}$): 3077 (Vinyl-H), 2980 (C—H), 2929 (C—H), 2857 (C—H), 1763 (C=O), 1640 (C=C), 1462 ($CH_2$), 1160 (C—O).

Surface Characterization Techniques—Diffuse Reflectance Infrared Fourier Transform Spectroscopy (DRIFT) were recorded using a Nicolet MAGNA-IR 860 spectrometer at 2 cm$^{-1}$ resolution. The porous silicon sample was mounted in a purged sample chamber with the light focused normal to the surface. Typically, 3000 scans were used to eliminate residual $CO_2$ and $H_2O$ vapour from the spectrum. X-ray photoelectron spectroscopy (XPS) spectra were recorded on a Kratos Axis instrument, using monochromated Al Ka (1486 eV) radiation with detection on the surface normal. The pressure during the analysis was ~5×10$^{-8}$ Torr.

Porous Silicon Etching Procedure: Heavily-doped p-type silicon wafers (<100>, Boron-doped, 0.0018–0.0022 Ω·cm, International Wafer Service) were used to prepare porous silicon samples by an anodic etch in ethanolic HF solution (HF:EtOH=3:1 v/v). Prior to the etching procedure, the wafers were cleaned with a 3:1 (v/v) of $H_2SO_4$:$H_2O_2$ for 30 minutes, rinsed with copious amounts of Millipore water and then immersed in HF solution for 1 minute. These wafers were dried under nitrogen and contacted on the back side with an In/Ga eutectic and mounted in a Teflon etching cell. Porous silicon layers were fabricated at 400 mA/cm² for 10 s in the absence of light using a Pt mesh counter electrode to ensure a homogeneous electric field. The etched wafer was removed from the cell, rinsed with copious amounts of EtOH and dried under a stream of nitrogen.

Figure 1:
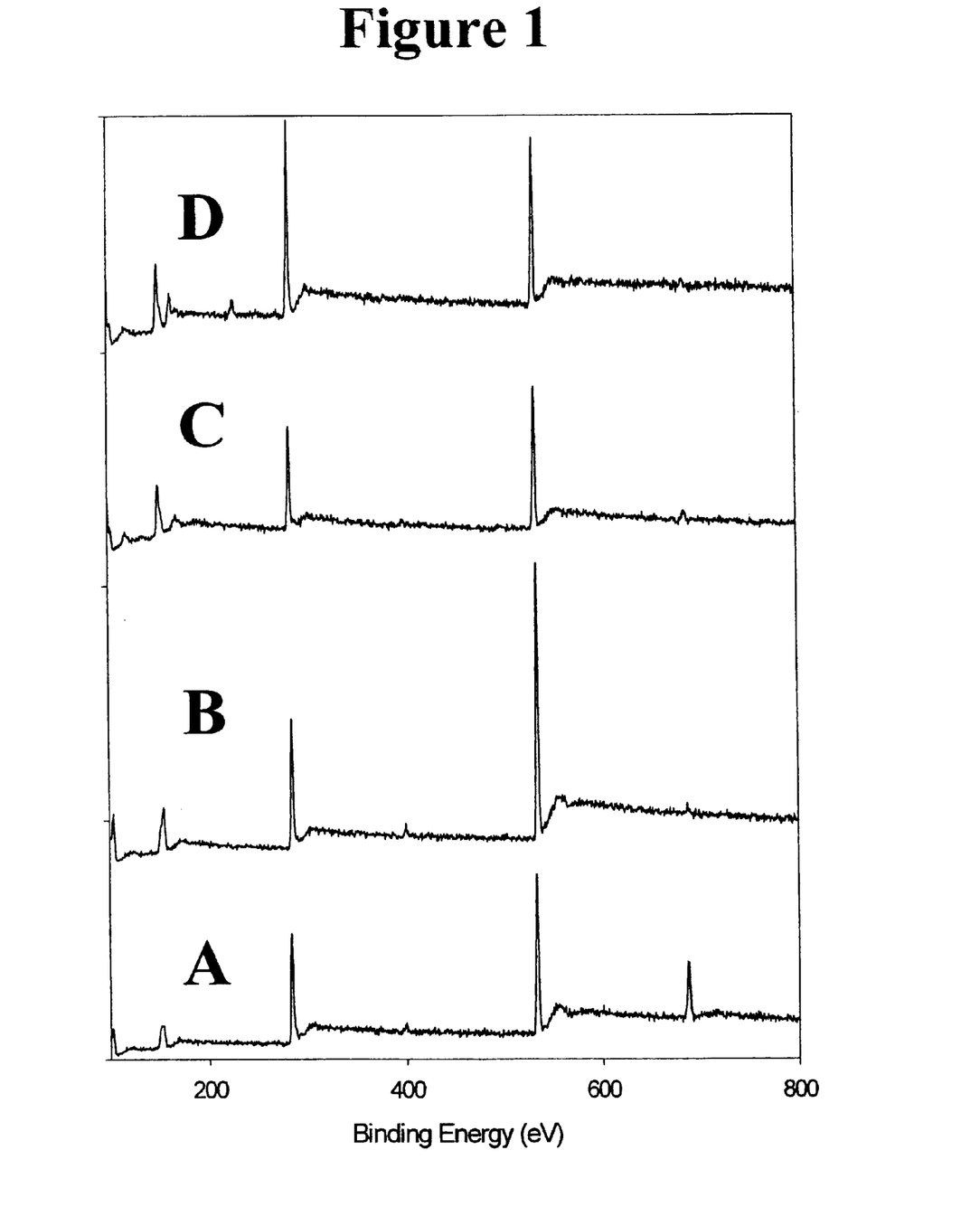
FIG. 1 shows X-ray photoelectron (XP) survey spectra of activated undecylenate ester layers on Porous silicon samples: (a) 2,2,2-trifluorethyl undecylenate IV; (b) 3-nitrophenyl undecylenate I; (c) N-succinimidyl undecylenate II; and (d) S-ethyl undecylenate III.
Figure 2:
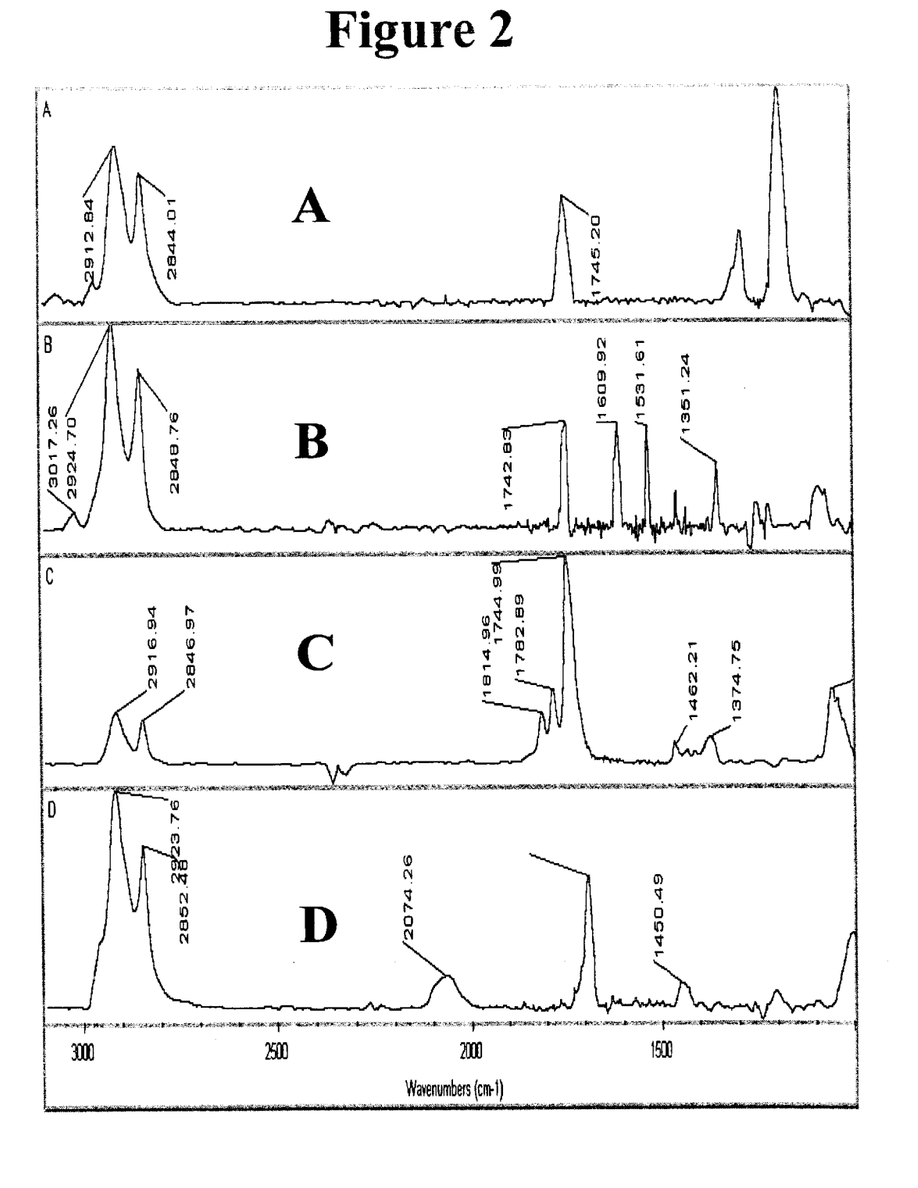
FIG. 2 shows diffuse reflectance FT-IR (DRIFT) spectra of a porous silicon layer after a thermal hydrosilylation reaction with: (a) 2,2,2-trifluorethyl undecylenate IV; (b) 3-nitrophenyl undecylenate I; (c) N-succinimidyl undecylenate II; and (d) S-ethyl undecylenate III.

Surface Modifications of Activated Esters I, II, III and IV layers on Porous Silicon—Stock solutions (0.3 M, n-heptane) of each of the activated esters I, II, III and IV were made up in a 25 mL volumetric flask. 5.0 mL aliquots of these solutions were degassed in a Schlenk tube with Ar for 30 minutes prior to the addition of the freshly prepared porous silicon surface. The Schlenk tube was heated to 120°C. for 18h after which the silicon wafer was removed, rinsed with copious amounts of THF and TCE, and dried under a stream of nitrogen. These monolayers were characterized by DRIFT and XPS analyses. XPS analyses are shown in FIG. 1. DRIFT analyses are shown in FIG. 2.

Amine Displacement Reactions—Three 100 mL stock solutions (1.0 mM) of n-butylamine, Me-Ala and Me-Cys were made up in a phosphorous buffered saline (PBS) solution of pH=7.4. A control solution was made without any amine. These solutions were stored at 0° C. in a refrigerator until use, when they were heated to 37° C. to mimic physiological conditions.

M-nitrophenyl undecylenic ester : Porous silicon surfaces modified with 3-nitrophenyl undecylenic ester I were immersed in: (a) 5 mL of the butylamine solution for 8 h in the dark and repeatedly checked by DRIFT every 2 hr over this time frame; (b) a solution of PBS (pH=7.4) irradiated at 254 nm with a Hg pen-lamp (7.4 mW/cm², Oriel Instruments) directly above the surface for 1 hr.

N-Succinimidyl undecylenic ester : Porous silicon surfaces with N-Succinimidyl ester undecylenic ester II were immersed in 5 mL of the Me-Ala solution for 8 h in the dark and repeatedly checked by DRIFT every 2 hr over this time frame. S-ethyl undecylenic ester: Porous silicon surfaces derivatized with S-ethyl undecylenic ester III were immersed in: (a) a 5 mL of the butylamine solution for 8 h and repeatedly checked by DRIFT every 2 hr over this time frame; (b) a 5 mL of the Me-Cys solution for 8 h in the dark and repeatedly checked by DRIFT every 2 hr over this time frame. The Me-Cys solution was pre-treated with 0.1 mL of an aqueous 10 mM DTT solution.

TFE/1-decene Dilution Studies via XPS: Freshly prepared hydrogen-terminated porous silicon surfaces were immersed in a Schlenk tube that was filled with varying molar ratios of TFE and 1-decene (1:1, 1:10 and 1:100). The solution was heated at 120° C. for 18 h, and rinsed with copious amounts of THF and TCE before drying under nitrogen. XPS analysis was used to determine the atomic ratios of carbon and fluorine on the surface. From this value, the relative ratio of TFE:1-decene on the surface was calculated.

Functionalization of Si<111>-H Surface With Undecylenic Acid Under Photochemical Conditions -continued

Figure 3:
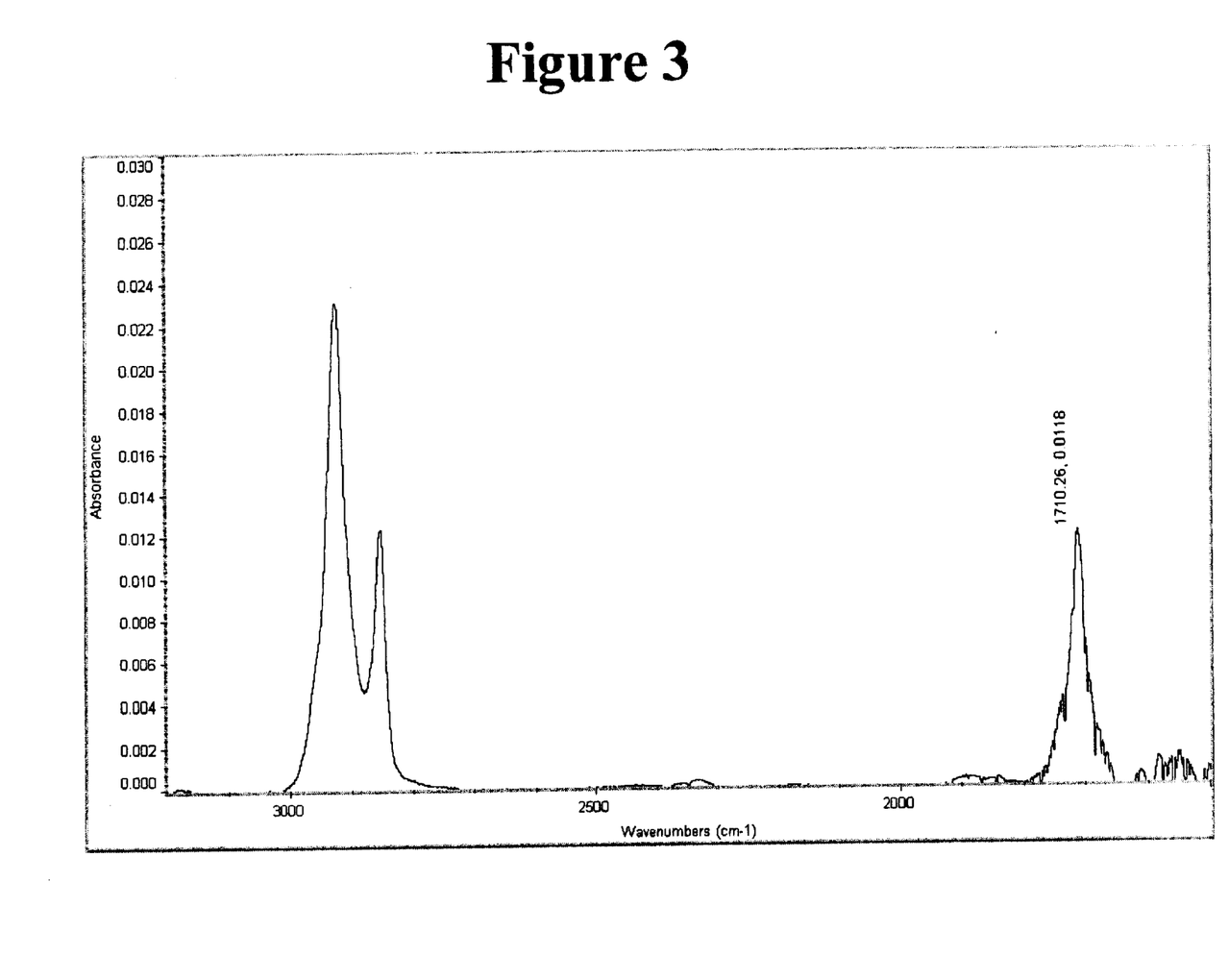
FIG. 3 shows an ATR-IR spectrum of Si—$C_{10}$COOH modified silicon surface using photochemical hydrosilylation of Si<111>—H and undecylenic acid in toluene.

A new Attenuated-Total-Reflection (ATR) Silicon <111> crystal was rinsed with water and immersed in a Piranha solution (3:1 $H_2SO_4:H_2O_2$) for 30 minutes at 80° C. The crystal was then removed and washed with Milli-Q water (Resistivity=$10^{18}$ Ωcm) before being placed into a teflon vial containing an etching solution of degassed 40% $NH_4F$ (clean room grade). After 17 minutes, the ATR crystal was removed from the etching solution, rinsed with Milli-Q water and transferred to a Schlenk tube that contained 10 ml. of a solution of toluene and undecylenic Acid (9:1 v/v%). After further degassing (45 min.) with Ar, the Schlenk tube was sealed and placed in a Rayonette photochemical chamber and irradiated (h>300 nm) for 3 hours. Once the Schlenk tube was removed, the ATR crystal was washed with copious amounts of tetrahydrofuran (THF) and 1,1,1-trichloroethane (TCE) to remove all physiorbed material. The resulting ATR crystal was characterized with ATR-IR spectroscopy (see FIG. 3) which shows the bands expected for a silicon surface with a layer that is terminated with COOH groups.

Activation of the COOH-Terminal Groups on Si<111>

Figure 4:
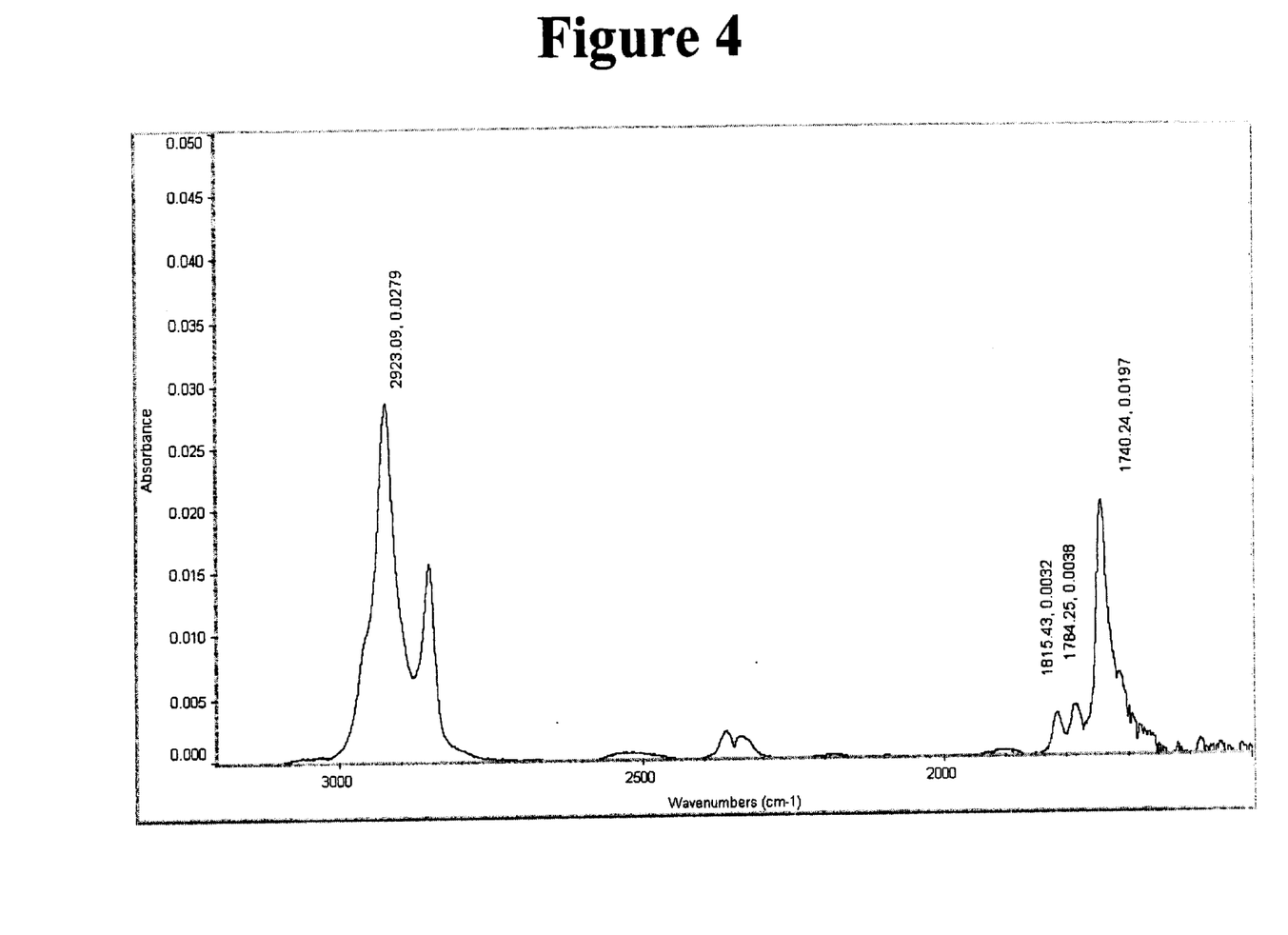
FIG. 4 shows an ATR-IR spectrum of Si—$C_{10}$CONHS modified silicon surface using the activating reagents NHS (N-hydroxysuccinimide) and a water-soluble carbodiimide (EDC).

An ATR crystal modified with undecylenic acid as above, was immersed in an aqueous solution that contained 200 L of N-Hydroxysuccinimide (NHS, 15 mM) and 200 L of 1-(3-dimethylaminopropyl)-3-ethylcarbodiimide.HCl (EDC, 20 mM) for 1 h. After removal, the crystal was washed with water and characterized using ATR-IR spectroscopy. The terminal COOH groups were completely converted to succinimidyl esters using this protocol and are activated towards nucleophilic displacement (see FIG. 4).

Immobilization of Biomolecules (ssDNA and Protein)

-continued

Figure 5:
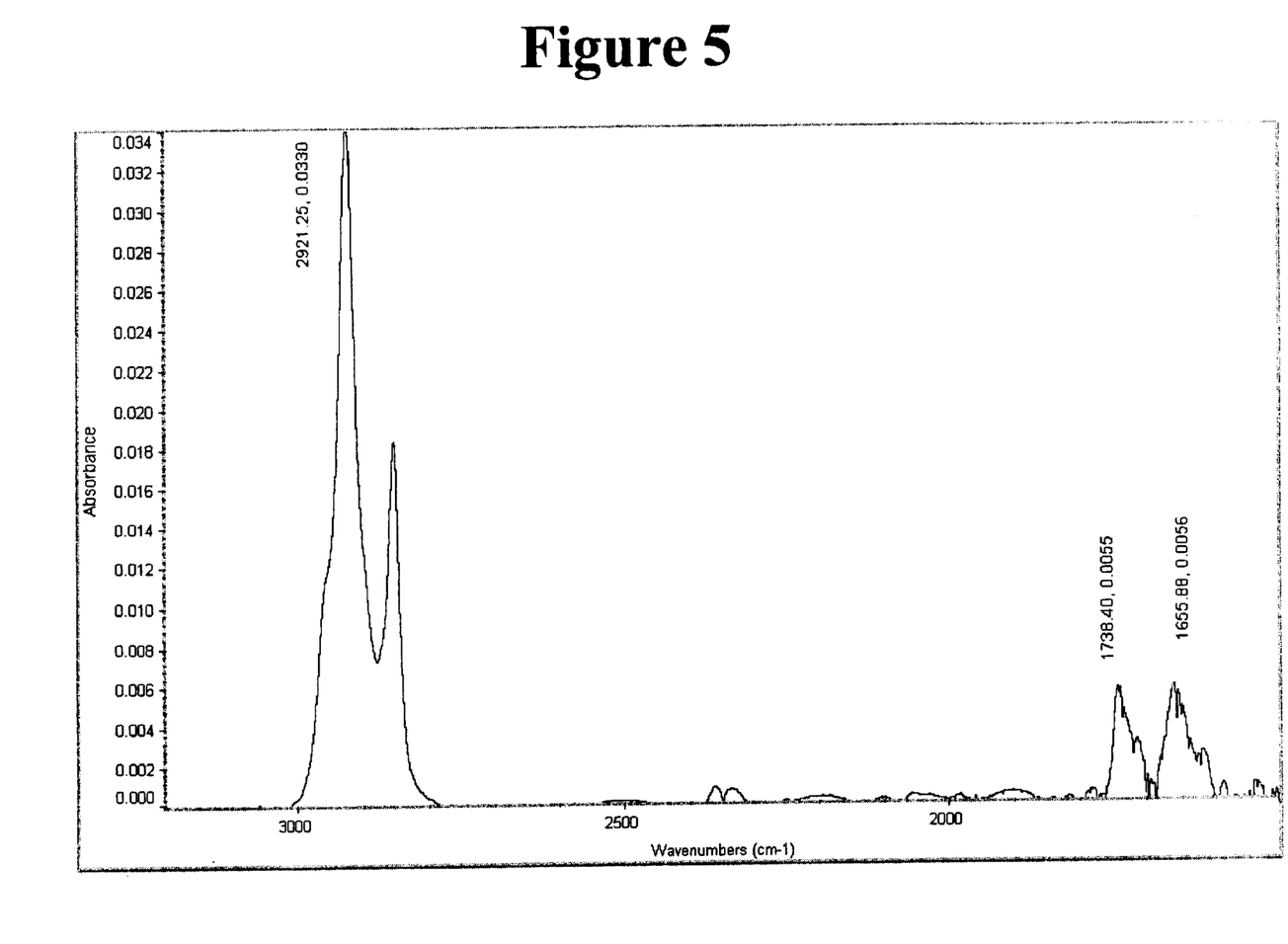
FIG. 5 shows an ATR element with amino$C_{12}$-modified ssDNA immobilized via the reaction of the primary amino group with the terminal activated succinimidyl moiety on Si<111>.
Figure 7:
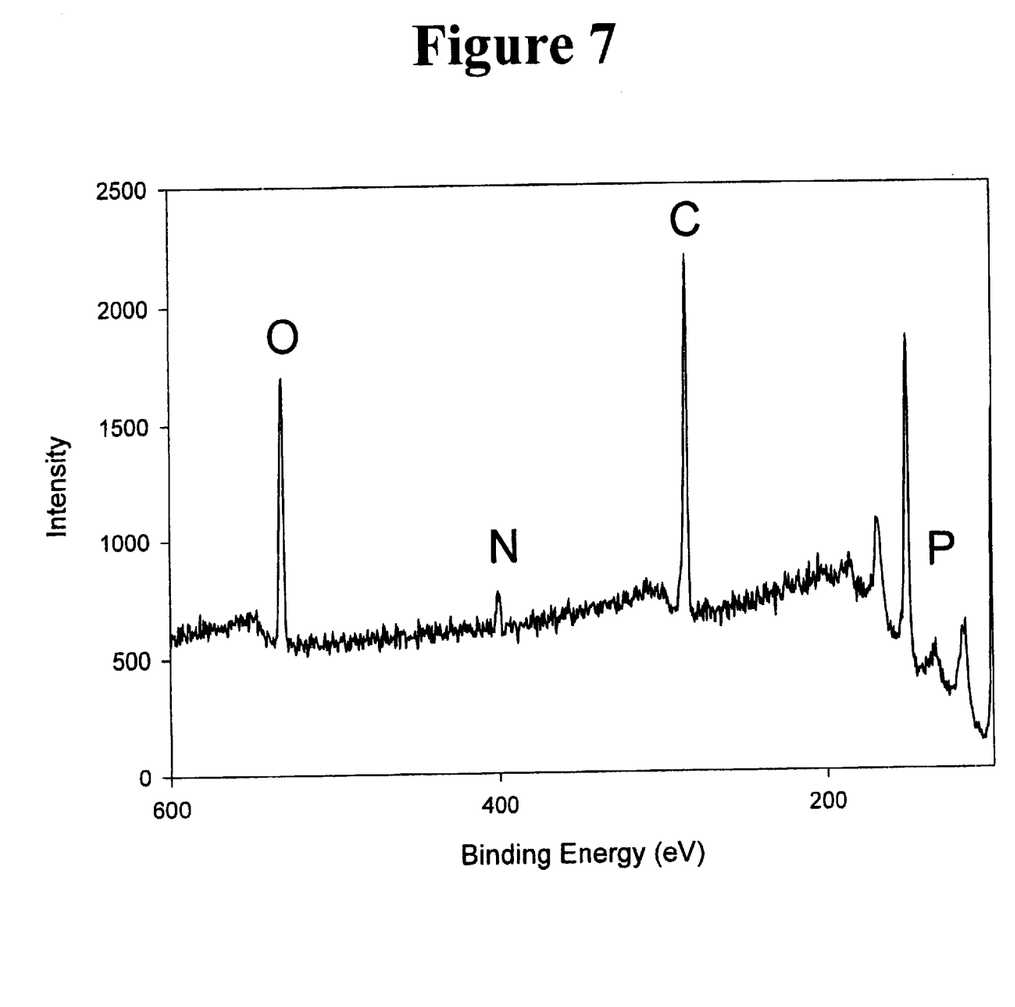
FIG. 7 shows an X-ray Photoelectron Spectrum of Si<111> modified with 5'—$H_2N$—$C_{12}$-TT-CCT-GTT-ACC-GTT-CGA-CTT-G-3'.

Immobilization of single-stranded DNA on an Si<111> surface An ATR crystal activated with NHS according to the above procedure, was immersed in 400 L of a PBS buffer solution containing single-stranded DNA tethered at the 5' end via a 12 carbon bridge to a primary amino group. (5'-H$_2$N—C$_{12}$-TT-CCT-GTT-ACC-GTT-CGA-CTT-G-3', [DNA}=20 nM). The solution was maintained at 25° C. for 3 h and then the ATR crystal was characterized using ATR-IR spectroscopy (see FIG. 5). The ATR crystal was further characterized using X-ray Photoelectron Spectroscopy (see FIG. 7).

Immobilization of a Phage-display Protein on an Si<111>Surface

Figure 6:
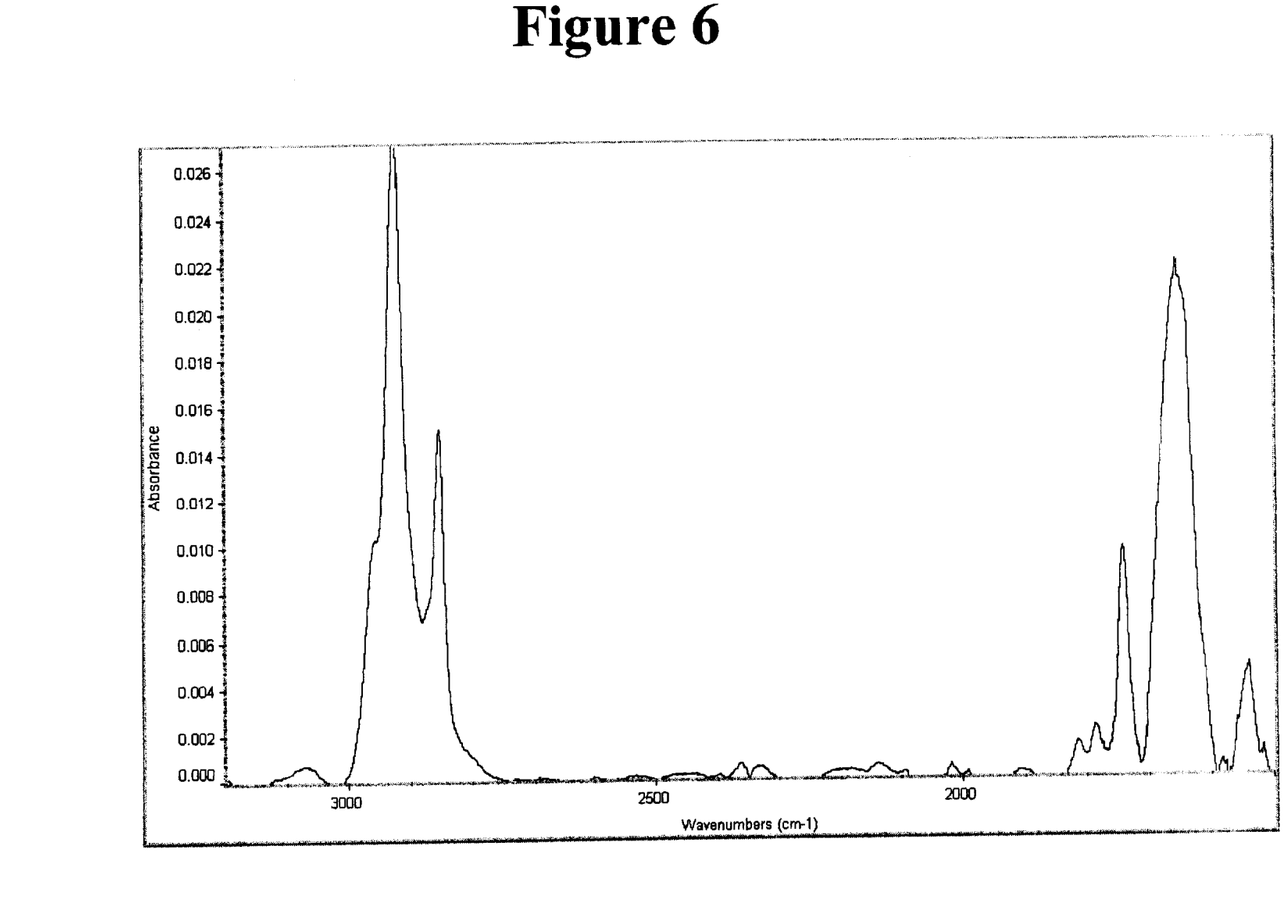
FIG. 6 shows an ATR element with a heavy chain lamda antibody immobilized via the reaction of a peripheral amino groups with the terminal activated succinimidyl moiety on Si<111>.
Figure 8:
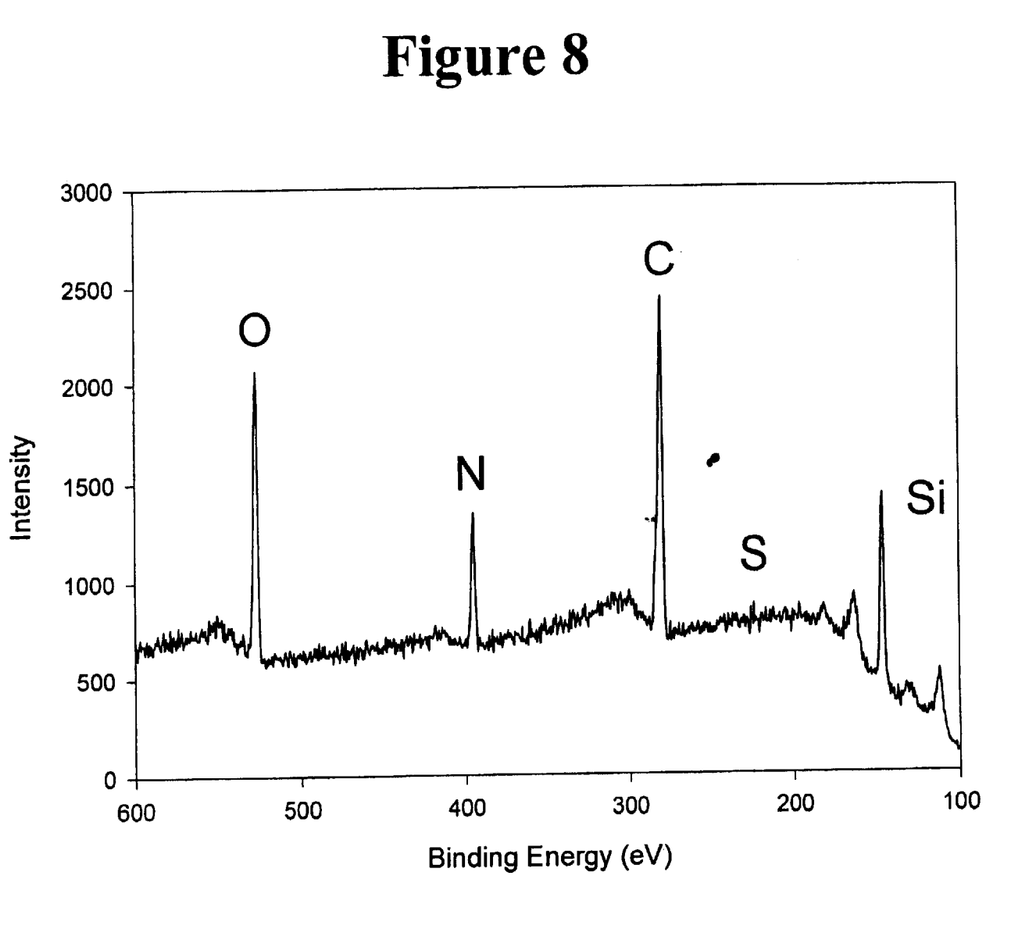
FIG. 8 shows an X-ray Photoelectron Spectrum of Si<111> modified with antibody.

An ATR crystal activated with NHS according to the above procedure was immersed in 400 L of a HEPES buffer solution that contained 150 mM NaCl, 0.2 mM EDTA and 5 mg/mL of a heavy chain variable domain lamda antibody (MW≈15000) that had been isolated using phage-display technology. The solution was maintained at 25° C. for 3 h and then the ATR element was characterized using ATR-IR spectroscopy (see FIG. 6). The ATR element was further characterized using X-ray Photoelectron Spectroscopy (see FIG. 8).

References (All of Which are Incorporated Herein by Reference

[1]Wagner, P.; Nock, S.; Spudich, J. A.; Volkmuth, W. D.; Chu, S.; Ciccro, R. L.; Wade, C. P. Linford, M. R.; Chidsey, C. E. D.; *J. Struct. Biol.* 1997, 119, 189–201.

[2] Bateman, J. E.; Eagling, R. D.; Worrall, D. R.; Horrocks, B. R.; Houlton, A.; *Alkylation of porous Silicon by Direct Reaction with Alkenes and Alkynes; Angew. Chem. Int. Ed.* 1998, 37, 2683–2685.

[3]Boukherroub, R.; Moring, S.; Bensebaa, F.; Wayner, D. D. M.; *New Synthetic Routes to Alkyl Monolayers on the Si(111)Surface; Langmuir* 1999, 15, 3831–3835.

[4]Buriak, J. M.; Allen, M. J.; *Lewis Acid Mediated Functionalization of Porous Silicon with Substituted Alkenes and Alkynes; J. Am. Chem. Soc.* 1998, 120, 1339–1340.

[5]Sieval, A. B.; Demirel, A. L.; Nissink, J. W. M.; Linford, M. R.; Maas, J. H. v.d.; Jeu, W. H. d.; Zuilhof, H.; Sudholter, E. J. R.; Langmuir 1998, 14, 1759–1768.

[6]Zhu, X.-Y.; Boiadjiev, J. A.; Mulder, J. A.; Hsung, R. P.; Major, R. C.; Molecular Assemblies on Silicon Surfaces via Si—O Linkages; Langmuir 2000; 16(17); 6766–6772.

[7]Zhu, X.-Y.; Mulder, J. A.; Bergerson, W. F.; *Chemical Vapour Deposition of Organic Monolayers on Si(100) via Si—N Linkages; Langmuir* 1999, 15, 8147–8154.

[8]Bergerson, W. F.; Mulder, J. A.; Hsung, R. P.; Zhu, X.-Y.; *Assembly of Organic molecules on Silicon Surfaces via the Si—N Linkage; J. Am. Chem. Soc.* 1999, 121, 454–455.

[9]Bansal, A.; Li, X.; Lauernan, I.; Lewis, N. S.; *J. Am. Chem. Soc.* 1996,118, 7225–7226.

[10]Boukherroub, R.; Bensebaa, F.; Morin, S.; Wayner, D. D. M.; *Langmuir* 1999, 15, 3831–3835.

[11]Effenberger, F.; Gotz, G.; Bidlingmaier, B.; Wezstein, M.; *Angew. Chem. Int. Ed.* 1998, 37, 2462–2464.

[12]Dancil, Keiki-Pua S.; Greiner, D. P.; Sailor, M. J.; "A Porous Silicon Optical Bio-sensor: Detection of Reversible Binding of IgG to a Protein A-modified Surface"; *J. Am. Chem. Soc.* 1999, 121, 7925–7930 (WEB published Aug. 13, 1999).

[13]Strother, T.; Cai, W.; Zhao, X.; Hamers, R. J.; Smith, L. M.; *J. Am. Chem. Soc.* 2000, 122, 1205–1209.

[14]Cullis, A. G.; Canham, L. T.; Calcon, P. D. J.; *J. Appl. Phys.* 1997, 82, 909–965

[15]Higashi, G. S.; Chabal, Y. J.; Trucks, G. W.; Raghavachari, K.; *Appl. Phys. Lett.* 1990, 12, 656.

[16]Wade, C. P.; Chidsey, C. E. D.; Appl. Phys. Lett. 1998, 71, 1679–1681.

[17]Boukherroub, R.; Moring, S.; Bensebaa, F.; Wayner, D. D. M.; *New Synthetic Routes to Alkyl Monolayers on the Si(111) Surface; Langmuir* 1999,15,3831–3835.

What is claimed is:

1. A method for immobilising a bio-molecule on a silicon substrate, the method comprising the steps:

(A) providing Si—H groups at a surface of the silicon substrate;

(B) attaching a bi-functional linker molecule having a coupling group that is unreactive with said silicon substrate and with bio-molecules until activation or deprotection and a CH$_2$=CH— group to the silicon substrate by reacting a Si—H group at said surface with the CH$_2$=CH— group of the linker molecule to form a covalent Si—C bond between said silicon substrate and said linker molecule, thus forming an attached linker molecule;

(C) modifying said coupling group of said attached linker molecule by activation or deprotection to make said coupling group ready for reaction with a bio-molecule to form an attached linker molecule having an reactive coupling group; and (D) covalently reacting said attached linker molecule having a reactive coupling group with a bio-molecule selected from the group consisting of a DNA, RNA, protein and carbohydrate, to immobilise said bio-molecule on said silicon substrate.

2. The method of claim 1, wherein the covalent bond to the surface is formed in a thermal reaction.

3. The method of claim 1, wherein the covalent bond to the surface is formed in a photochemical reaction.

4. The method of claim 1, wherein the silicon substrate is porous silicon.

5. The method of claim 1, wherein said unactivated functionality comprises a carboxyl radical.

6. The method of claim 5, wherein carboxyl radical is activated by reaction with N-hydroxysuccinimide.

* * * * *